(12) United States Patent
Mordaunt

(10) Patent No.: US 11,260,135 B2
(45) Date of Patent: Mar. 1, 2022

(54) DYE ENHANCED VISUALIZATION OF CATARACT SURGERY

(71) Applicant: EOS HOLDINGS, LLC, Los Gatos, CA (US)

(72) Inventor: David Mordaunt, Los Gatos, CA (US)

(73) Assignee: Excel-Lens, Inc., Los Gatos, CA (US)

(*) Notice: Subject to any disclaimer, the term of this patent is extended or adjusted under 35 U.S.C. 154(b) by 385 days.

(21) Appl. No.: 15/953,310

(22) Filed: Apr. 13, 2018

(65) Prior Publication Data
US 2019/0314529 A1 Oct. 17, 2019

(51) Int. Cl.
| | |
|---|---|
| *A61K 9/48* | (2006.01) |
| *A61K 49/00* | (2006.01) |
| *A61K 9/00* | (2006.01) |
| *A61K 9/08* | (2006.01) |
| *A61B 34/30* | (2016.01) |
| *A61F 2/16* | (2006.01) |
| *A61F 9/008* | (2006.01) |

(52) U.S. Cl.
CPC ............ *A61K 49/006* (2013.01); *A61B 34/30* (2016.02); *A61F 2/1662* (2013.01); *A61F 9/008* (2013.01); *A61K 9/0048* (2013.01); *A61K 9/08* (2013.01); *A61B 2218/002* (2013.01); *A61B 2218/007* (2013.01); *A61F 2009/00889* (2013.01)

(58) Field of Classification Search
None
See application file for complete search history.

(56) References Cited

U.S. PATENT DOCUMENTS

| | | | | |
|---|---|---|---|---|
| 6,367,480 B1* | 4/2002 | Coroneo | ................ | A61B 90/39 |
| | | | | 128/898 |
| 6,720,314 B1* | 4/2004 | Melies | ................ | A61P 41/00 |
| | | | | 514/150 |

OTHER PUBLICATIONS

B. Braun Medical, Inc. (available online at https://dailymed.nlm.nih.gov/dailymed/fda/fdaDrugXsl.cfm?setid=f47d4c31-8871-74dd-2e13-52af971a69e0&type=display, Dec. 2018) (Year: 2018).*
Morales et al (Invest Ophthamol Vis Sci 51:6018-6029, 2010) (Year: 2010).*
Brockmann T, Steger C, Dawczynski J. Photodynamic Properties of Vital Dyes for Vitreoretinal Surgery, Ophthalmologica 2012; 228: 234-238.
Melles GR, De Waard PWT, Pameyer JH, et al. Trypan blue capsule staining to visualize the capsulorhexis in cataract surgery. J Cataract Refract Surg 1999;25: 7-9.
Jhanji V, Chan E, Das S, et al. Trypan blue for anterior segment surgeries, Eye (Lond). Sep. 2011; 25(9): 1113-1120.
Rodrigues EB, Costa EF, Penha FM, et al. The Use of Vital Dyes in Ocular Surgery, Survey of Ophth., 54 (5), 576-617 (2009).
Rodrigues EB, Meyer CH, Kroll P. Chromovitrectomy: a new field in vitreoretinal surgery Graefes Arch Clin Exp Ophthalmol 2005; 243:291-293.
Aguilera Teba F, Mohr A, Eckardt C, et al. Trypan blue staining in vitreoretinal surgery. Ophthalmology 2003; 110:2409-2412.
Sousa-Martins D, Caseli L, Figueiredo M, et al. Comparing the mode of action of intraocular lutein-based dyes with synthetic dyes. IOVS 2015.
Narayanan R, Kenney MC, Kamjoo S, et al. Trypan blue: effect on retinal pigment epithelial and neurosensory retinal sells. Invest Ophthalmol Vis Sci 2005; 46: 304-309.
Jin Y, Uchida S, Yanagi Y, et al. Neurotoxic effects of Trypan blue on rat retinal ganglion cells. Exp Eye Res 2005:81:395-400.
Stalmans P, Van Aken EH, Melles G, et al. Trypan blue not toxic for retinal pigment epithelium in vitro. Am J Ophthalmol 2003; 135:234-236.
Gale JS, Proulx AA, Gonder JR, et al. Comparison of the in vitro toxicity of indocyanine green to that of Trypan blue in human retinal pigment epithelium cell cultures. Am J Ophthalmol 2004; 138: 64-69.
Mennel S, Thumann G, Peter S, et al. Influence of vital dyes on the function of the outer blood-retinal barrier in vitro. Klin Monatsbl Augenheilkd 2006; 223: 568-576.
Kwok AKH, Yeung C-K, Lai TYY, et al. Effects of Trypan blue on cell viability and gene expression in human retinal pigment epithelial cells. Br J Ophthalmol 2004; 88: 1590-1594.
Rezai KA, Farrokh-Siar L, Gasyna EM, et al. Trypan blue induces apoptosis in human retinal pigment epithelial cells. Am J Ophthalmol 2004; 138: 492-495.
Hirasawa H, Yanagi Y, Tamaki Y, et al. Indocyanine green and Trypan blue: intracellular uptake and extracellular binding by human retinal pigment epithelial cells. Retina 2007; 27: 375-378.
Costa E. F, Barros NLT, Coppini LP, et al., Effects of Light Exposure, pH, Osmolarity, and Solvent on the Retinal Pigment Epithelial Toxicity of Vital Dyes, Am J Ophthalmol 2013; 155: 705-712.
Awad D, Schrader I, Bartok M, et al. Comparative toxicology of Trypan blue, brilliant blue G, and their combination together with polyethylene glycol on human pigment epithelial cells. Investigative Ophthalmology & Visual Science 2011; 52(7): 4085-4090.
Costa E.F, et al., Viatal Dyes and Light Sources for Chromovitrectomy: Comparative Assesment of Osmolarity, pH, and Spectrophotometry, Investigative Ophthalmology & Visual Science, Jan. 2009, vol. 50, No. 1, 385-391.
J.P. Graham, et al., Experimental and theoretical study of the spectral behavior of Trypan Blue in various solvents, Journal of Molecular Structure 1040 (2013) 1-8.
Delori et al., Spectral reflectance of the human ocular fundus, Applied Optics, Mar. 15, 1989, vol. 28, No. 6, 1061-1077.

* cited by examiner

*Primary Examiner* — Craig D Ricci
(74) *Attorney, Agent, or Firm* — Schmidt Patent Law, Inc.

(57) ABSTRACT

The invention relates generally to the use of dyes to enhance visualization of tissues and boundaries of openings in tissues during cataract surgery.

12 Claims, 15 Drawing Sheets
(7 of 15 Drawing Sheet(s) Filed in Color)

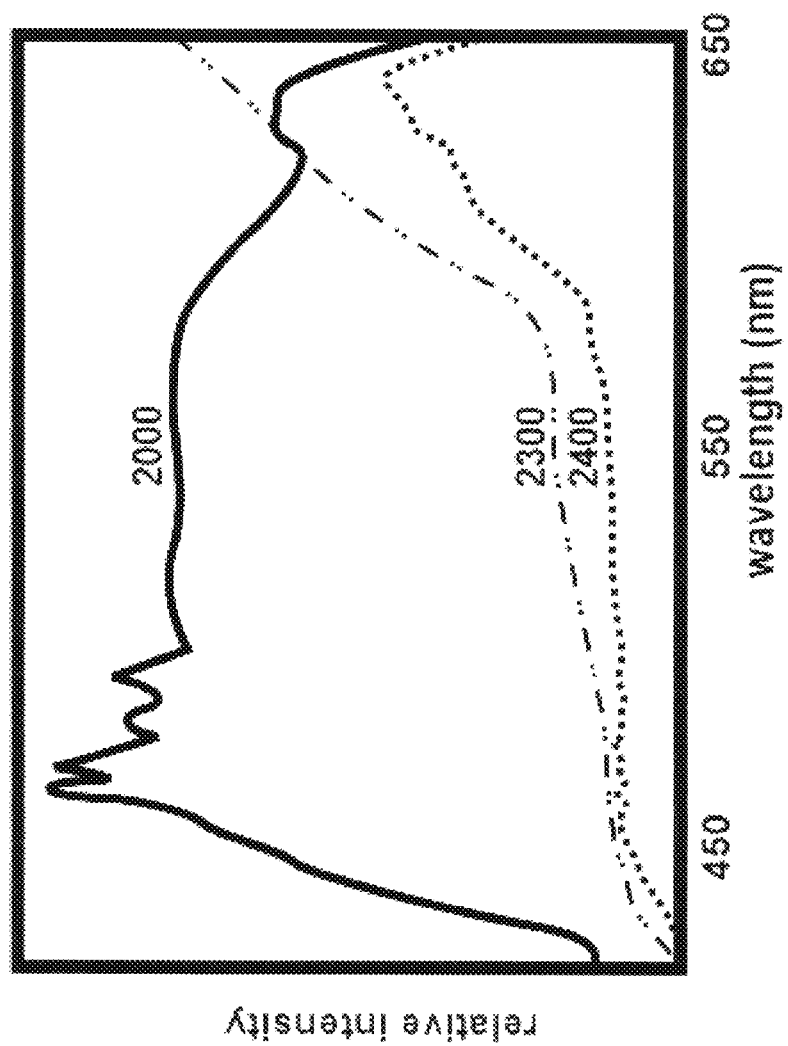

DYE ENHANCED VISUALIZATION OF CATARACT SURGERY

FIELD OF THE INVENTION

The invention relates generally to the use of dyes to enhance visualization of tissues and boundaries of openings in tissues during cataract surgery.

BACKGROUND

In surgery, visualization of tissues and boundaries is a necessary condition for consistent success and to minimize complications. In cataract surgery visualization of the anterior capsule and the capsulotomy rim is critical for all stages of the surgery, specifically during formation of the capsulotomy, crystalline lens removal, cortical clean-up and intraocular lens (IOL) insertion.

Trypan Blue is a vital dye first synthesized in 1904. Trypan Blue belongs to the anionic diazo family of vital dyes with the chemical formula $C_{34}H_{24}N_6Na_4O_{14}S_4$ and a molecular weight of 960. This organic compound has the chromophore and functional group R—N=N—R', which provides the light absorbing properties of the dye, in which R and R' are aromatic hydrocarbons. The blue dye is blue in appearance because red and orange light are strongly absorbed. Trypan blue dissolved in a neutral pH aqueous solution has its maximum absorption in the orange region of the spectrum about 590 nm. [1]

Live cells or tissues with intact cell membranes are not colored by Trypan Blue because the cell membranes in living cells do not stain with the blue dye molecule. However, Trypan Blue stains dead cells and collagen membranes. Hence, dead cells and collagen membranes are shown in a distinctive blue color under a microscope. Since live cells are excluded from staining, this staining method is also described as a dye exclusion method and is used in histology.

Trypan Blue is frequently used in ocular surgery. Since the late 1990s, Trypan Blue with a concentration of equal or less than 0.06% by weight has demonstrated significant affinity properties for the anterior lens capsule and showed an ability to improve visualization by color staining in cataract surgery to facilitate capsulotomy, especially in patients with a white (opaque) cataract. [2-4] Capsulotomy is the formation of an approximately central continuous circular or elliptical opening in the anterior or posterior lens capsule. Also, vitreoretinal surgeons started the intraoperative application of different dyes to identify membranes and tissues of interest in vitreoretinal surgery. Trypan Blue in a concentration of equal or less than 0.15% is known to stain the acellular internal limiting membrane (ILM) and the glial epiretinal membrane (ERM) in dye enhanced vitreoretinal surgery, also known as chromovitrectomy [5, 6]. No pharmacological, immunological or metabolic means is involved in the Trypan Blue staining process, i.e., no covalent bonds to the dye are formed. [7]

U.S. Pat. No. 6,720,314 to Melles discloses the use of Trypan Blue for visualization during cataract surgery at concentrations of 0.001 to 2.0% with a preferred concentration of 0.1%, and with contrast between stained and unstained tissues based on color. Melles teaches that Trypan Blue does not diffuse into the lens capsule.

U.S. Pat. No. 6,367,480 to Coroneo discloses the use of Trypan Blue for visualization during cataract surgery at concentrations of 0.05 to 3.0% with a preferred concentration of 0.1%, also with contrast between stained and unstained tissues based on color.

A literature review [8-17] of Trypan Blue as an intraocular dye concludes that Trypan Blue is safe for intraocular use at a concentration of up to 0.5% with an exposure time limited to no more than 5 minutes, yet at longer exposure times, such as 30 minutes, a concentration of 0.25% is toxic to sensitive intraocular cells. [17] In cataract surgery the dye solution is typically in the eye for one minute or less, for example 10 seconds, before it is diluted by a rinse and then washed out. However, the stained capsule locally maintains at least 60% of the original concentrations of trypan blue for an hour or longer following surgery.

Hence the higher ends of the concentration ranges disclosed by Melles and Coroneo are disfavored by prior art teachings because residual dye would remain in the eye at concentrations and for durations exceeding toxicity limits.

REFERENCES

1. Brockmann T, Steger C, Dawczynski J. Photodynamic Properties of Vital Dyes for Vitreoretinal Surgery, Ophthalmologica 2012; 228: 234-238.
2. Melles G R, De Waard P W T, Pameyer J H, et al. Trypan blue capsule staining to visualize the capsulorhexis in cataract surgery. J Cataract Refract Surg 1999; 25: 7-9.
3. Jhanji V, Chan E, Das S, et al. Trypan blue for anterior segment surgeries, Eye (Lond). 2011 September; 25 (9): 1113-1120.
4. Rodrigues E B, Costa E F, Penha F M, et al. The Use of Vital Dyes in Ocular Surgery, Survey of Ophth., 54 (5), 576-617 (2009).
5. Rodrigues E B, Meyer C H, Kroll P. Chromovitrectomy: a new field in vitreoretinal surgery. Graefes Arch Clin Exp Ophthalmol 2005; 243:291-293.
6. Aguilera Teba F, Mohr A, Eckardt C, et al. Trypan blue staining in vitreoretinal surgery. Ophthalmology 2003; 110: 2409-2412.
7. Sousa-Martins D, Caseli L, Figueiredo M, et al. Comparing the mode of action of intraocular lutein-based dyes with synthetic dyes. IOVS 2015.
8. Narayanan R, Kenney M C, Kamjoo S, et al. Trypan blue: effect on retinal pigment epithelial and neurosensory retinal cells. Invest Ophthalmol Vis Sci 2005; 46: 304-309.
9. Jin Y, Uchida S, Yanagi Y, et al. Neurotoxic effects of Trypan blue on rat retinal ganglion cells. Exp Eye Res 2005:81: 395-400.
10. Stalmans P, Van Aken E H, Melles G, et al. Trypan blue not toxic for retinal pigment epithelium in vitro. Am J Ophthalmol 2003; 135: 234-236.
11. Gale J S, Proulx A A, Gonder J R, et al. Comparison of the in vitro toxicity of indocyanine green to that of Trypan blue in human retinal pigment epithelium cell cultures. Am J Ophthalmol 2004; 138: 64-69.
12. Mennel S, Thumann G, Peter S, et al. Influence of vital dyes on the function of the outer blood-retinal barrier in vitro. Klin Monatsbl Augenheilkd 2006; 223: 568-576.
13. Kwok A K H, Yeung C-K, Lai T Y Y, et al. Effects of Trypan blue on cell viability and gene expression in human retinal pigment epithelial cells. Br J Ophthalmol 2004; 88: 1590-1594.
14. Rezai K A, Farrokh-Siar L, Gasyna E M, et al. Trypan blue induces apoptosis in human retinal pigment epithelial cells. Am J Ophthalmol 2004; 138: 492-495.

15. Hirasawa H, Yanagi Y, Tamaki Y, et al. Indocyanine green and Trypan blue: intracellular uptake and extracellular binding by human retinal pigment epithelial cells. Retina 2007; 27: 375-378.

16. Costa E. F, Barros N L T, Coppini L P, et. Al., Effects of Light Exposure, pH, Osmolarity, and Solvent on the Retinal Pigment Epithelial Toxicity of Vital Dyes, Am J Ophthalmol 2013; 155: 705-712.

17. Awad D, Schrader I, Bartok M, et al. Comparative toxicology of Trypan blue, brilliant blue G, and their combination together with polyethylene glycol on human pigment epithelial cells. Investigative Ophthalmology & Visual Science 2011; 52(7): 4085-4090.

SUMMARY

The inventor has discovered that Trypan Blue dye may be used to enhance visualization during cataract surgery without toxic effects at high concentrations that the prior art disfavors because of expected toxicity at those concentrations. The inventor has further discovered that the use of Trypan Blue at these higher concentrations advantageously provides faster and darker staining of anterior and posterior lens capsule tissue and improved visualization of tissues and tissue boundaries, compared to the lower preferred concentrations taught in the prior art.

In one aspect, an ophthalmic solution for enhancing visualization during cataract surgery comprises an isotonic and pH neutral aqueous solution of Trypan Blue at a concentration of 0.2 to 0.45% by weight. The solution may comprise 0.7% by weight NaCl, for example. The solution may be applied to the lens capsule to improve visualization of the anterior lens capsule, posterior lens capsule, capsulotomy boundary, corneal incisions, and lens epithelial cells by decreasing the intensity of light transmitted through the tissue containing Trypan Blue.

In another aspect, the Trypan Blue ophthalmic solution described above is used in a method to enhance visualization of tissue and tissue boundaries during cataract surgery. The method comprises applying the dye solution to the lens capsule for a time period of less than a minute, for example less than or equal to 10 seconds, to stain the lens capsule, then promptly rinsing the unabsorbed dye solution from the eye. After staining and rinsing, a capsulotomy may be performed in the anterior and/or posterior lens capsule. The stained lens capsule temporarily retains the dye, which is gradually washed out over a period of a few hours. The local dye concentration in the lens capsule may exceeds the toxicity concentrations observed in the prior art. [17]

In the above method, stained tissues (e.g., anterior and posterior lens capsule) may be distinguished from each other and from boundaries of the tissues (e.g., the boundary of a capsulotomy) by the intensity of light transmitted through the tissues, for example by the intensity of red light reflected from the retina and transmitted through the lens capsule, in addition to or instead of by differences in the color between stained and unstained tissue. This enhances visualization of the tissues and openings, compared to prior art methods. In contrast to the teaching of Melles and as further discussed below, the inventor has found that Trypan Blue diffuses into and through the lens capsule. Consequently, the apparent darkness (reduction in transmitted intensity) of a stained lens capsule tissue increases with the concentration of Trypan Blue in the staining solution and with the thickness of the tissue.

As further explained below, use of Trypan Blue in the specified concentration range to stain the lens capsule is unexpectedly safe for tissues in the eye specifically in the region of the lens capsule.

These and other embodiments, features, and advantages of the present invention will become more apparent to those skilled in the art when taken with reference to the following more detailed description of the invention in conjunction with the accompanying drawings that are first briefly described.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 10 shows plots of a typical Xenon bulb spectrum, the retina reflectance and the spectrum of light from the Xenon bulb reflected from the retina.

DETAILED DESCRIPTION

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise.

Figure 1:
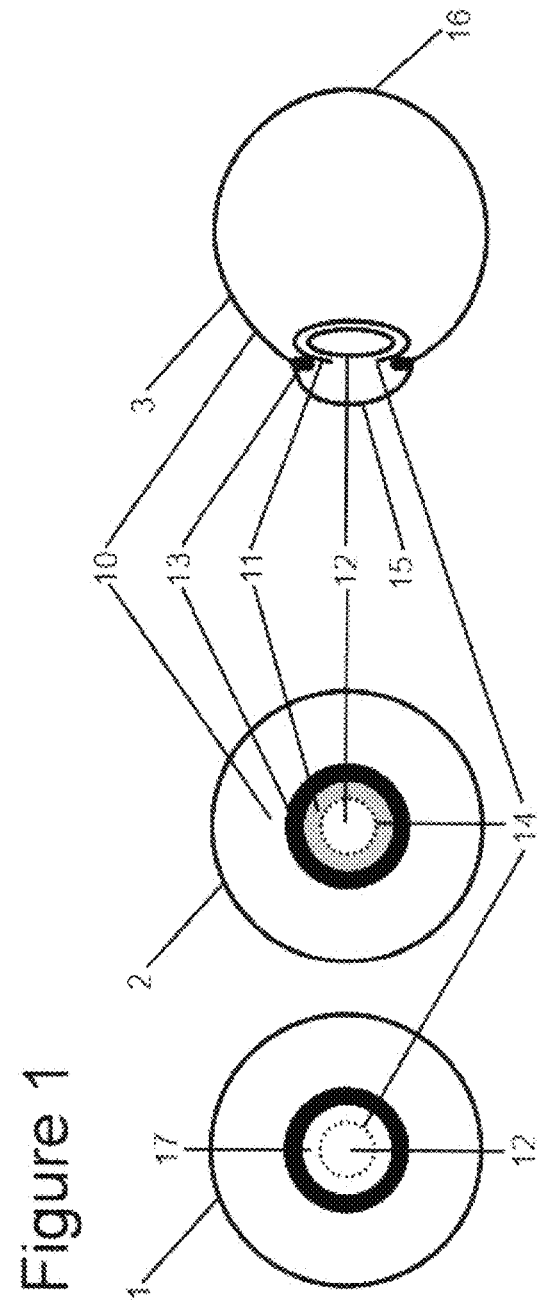
FIG. 1 illustrates the anatomy of the eye in anteroposterior (AP) and cross-sectional views.

FIG. 1 illustrates the anatomy of the eye in an AP view 1 of an eye with an unstained anterior capsule and capsulotomy, an AP view 2 of an eye with a dye-stained anterior capsule stained by the dye solution and the method described above and a capsulotomy, and a cross-sectional view 3 in the sagittal plane of either eye. These figures show the sclera 10, an anterior capsule stained with Trypan Blue dye 11, the center of the capsulotomy region 12, the iris 13, the capsulotomy rim 14, the cornea 15, the retina 16, and the unstained anterior capsule 17. The stained capsule 11 is noticeably darker (less light intensity) than the unstained capsule 17, which increases the visibility of the capsulotomy rim 14.

Figure 2:
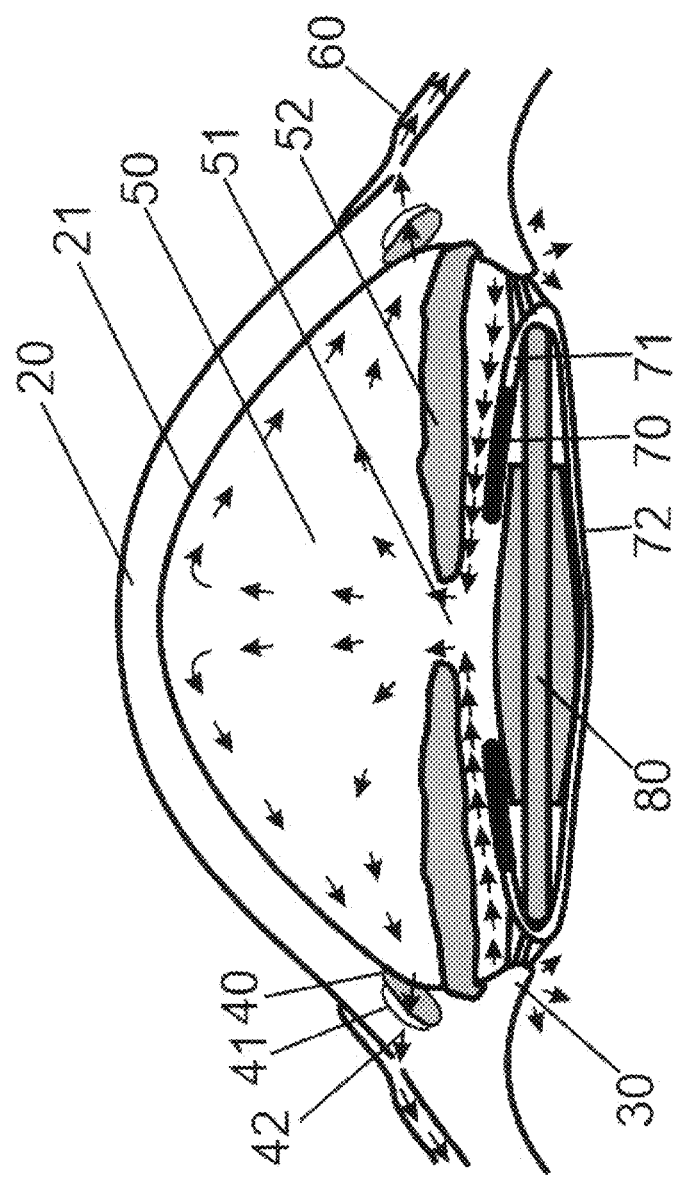
FIG. 2 shows another cross-sectional view of the eye.

FIG. 2 illustrates another cross-sectional view of a portion of an eye, showing cornea 20, corneal endothelial cells 21, ciliary process 30, trabecular meshwork 40, Schlemm's canal 41, collector channel 42, anterior chamber 50, pupil 51, iris 52, conjunctiva 60, anterior capsule stained with dye 70, unstained anterior capsule 71, and intraocular lens 80. The arrows show the natural flow of aqueous humor in the eye.

Figure 3:
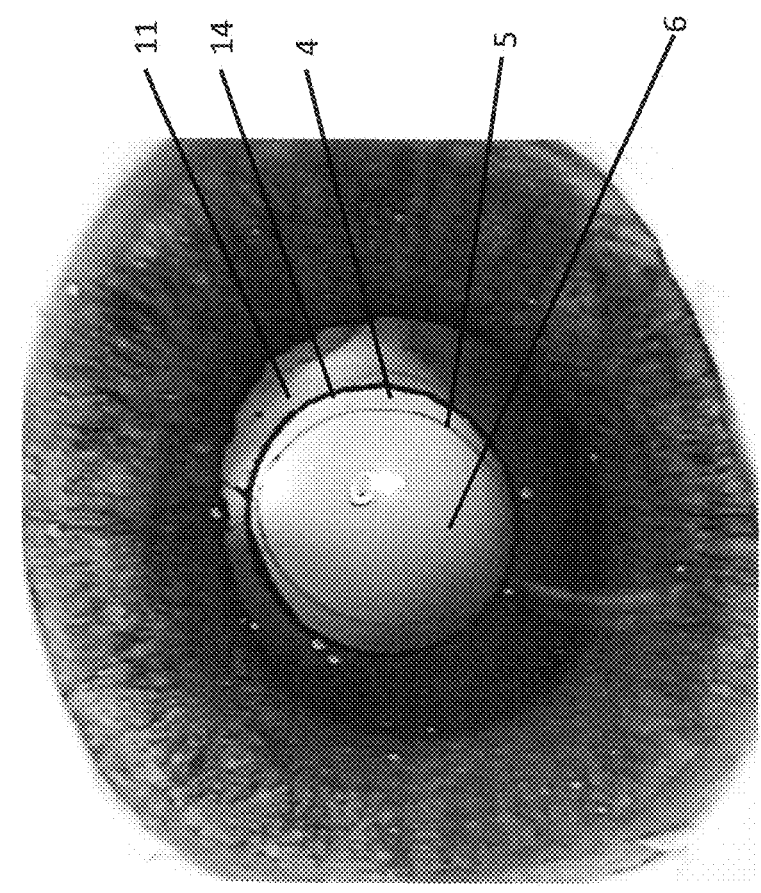
FIG. 3 is a photograph in which capsulotomies have been performed in the anterior and the posterior lens capsule after staining the lens capsule with Trypan Blue.

FIG. 3 is a photograph of an eye in which a capsulotomy has been performed in the anterior lens capsule and another in the posterior lens capsule, after staining the lens capsule with Trypan Blue by the method described above. This photograph shows stained anterior lens capsule 11, stained anterior capsulotomy rim 14 with a dark rolled-over edge, stained posterior capsule 4, stained posterior capsulotomy rim 5 with a dark rolled-over edge, and transparent central region 6 looking through the anterior and posterior capsulotomies. The various tissues and boundaries of openings may be distinguished by their darkness, i.e., by the relative intensities of light transmitted through them, rather than by color.

Referring again to FIG. 2, in the method described above, the Trypan Blue dye solution is introduced into the anterior chamber 50 for a period of typically less than one minute, then rinsed from the eye. Immediately after the rinse and for approximately an hour or more afterward, the stained portion of the anterior lens capsule will typically comprise Trypan Blue dye at a concentration of at least 60% of that of the original concentration of the staining dye solution. Over a few hours, and completely within 24 hours, the staining dye naturally washes out of the stained portions of the lens capsule and out of the eye with the flow of aqueous humor in the eye. As the dye slowly washes out, the concentration of dye in the anterior chamber is small, for example less than 1% of the original dye solution concentration.

The concentration of dye in the acellular lens capsule would typically be toxic to cells in its proximity. However, the lens capsule consists of type IV collagen, not living cells. Thus, a locally high concentration for times in excess of 30 minutes in the collagen IV matrix of the lens capsule does not harm the lens capsule.

Further, the inventor has recognized that the most sensitive cells in the eye are cells in the retina and corneal endothelial cells. These cells are all distant from the lens capsule. For example, the corneal epithelium is nominally at least 2 mm away from the anterior capsulotomy. As dye molecules slowly wash out of the lens capsule at low concentration, they are further diluted as the flow enters the anterior chamber via the pupil. As a result, corneal endothelial cells may be exposed to Trypan Blue at less than 1% of the original solution concentration, for example. The sensitive retina cells are even more distant and are not directly involved in the outflow of the aqueous humor, thus will have even less exposure than 0.1% of the original solution concentration. Consequently, even though the lens capsule comprises dye at locally high concentrations, the most sensitive cells in the eye are not exposed to such high (toxic) concentrations of the dye.

The inventor has experimentally determined that the toxicity threshold is at a Trypan Blue staining solution concentration of at least 0.5%. Further, the inventor has performed preclinical and clinical testing including over 400 capsulotomies utilizing the Trypan Blue solution and staining method described above with no adverse event and no increased cell death when compared with a control group of cataract patients which received surgery with capsulotomy absent the use of Trypan Blue.

Thus, contrary to what one would expect from the toxicity concerns raised in the prior art, controlled experiments have determined that use of a Trypan Blue solution at concentrations of 0.25 to 0.45% by weight to stain the lens capsule is safe.

Figure 4:
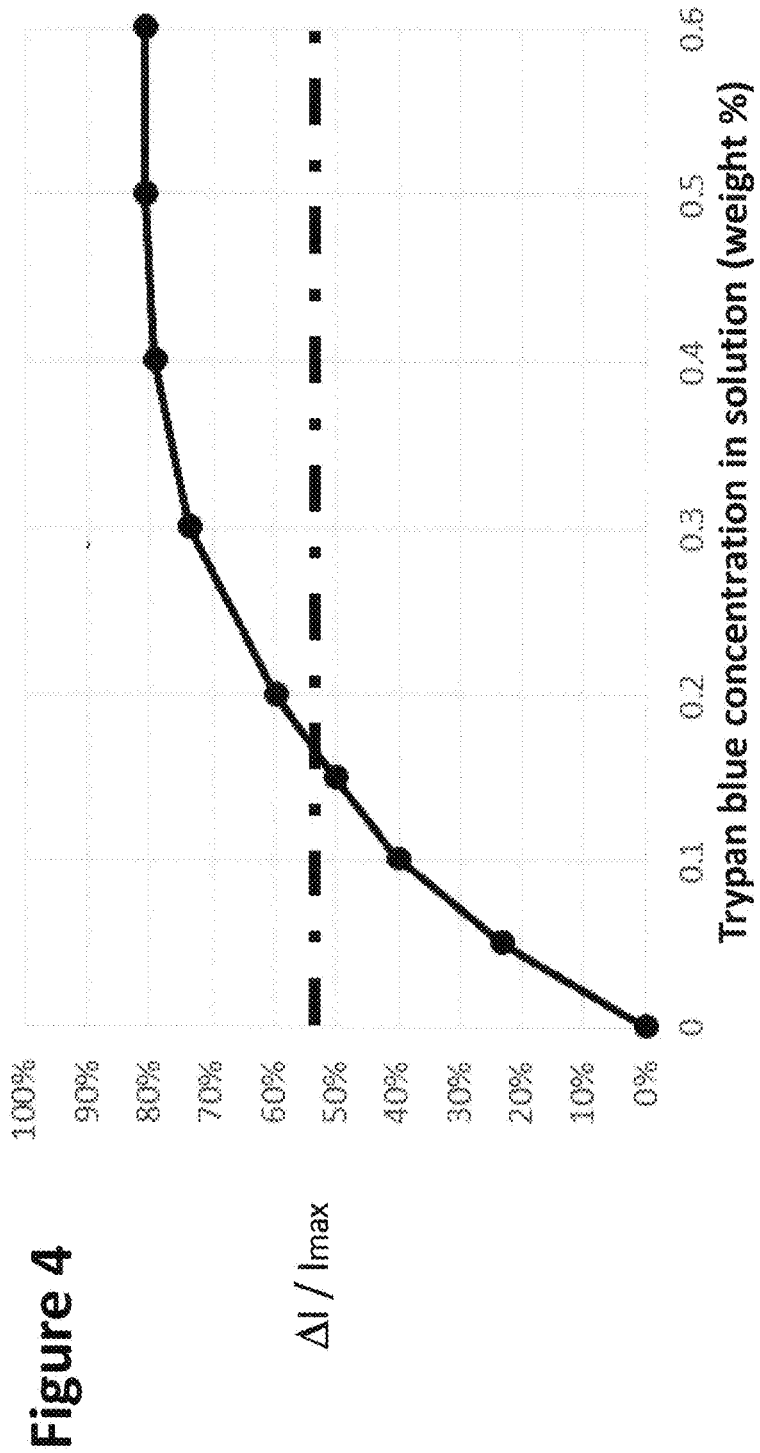
FIG. 4 plots the normalized change in light intensity $\Delta I/I_{max}$ transmitted through a stained anterior lens capsule as a function of Trypan Blue staining solution concentration.

Referring to FIG. 4, the inventor has experimentally determined the normalized change in light intensity $\Delta I/I_{max}$ (solid curve with circles) transmitted through the stained anterior lens capsule as a function of Trypan Blue staining solution concentration under white light illumination at levels typical for cataract surgery. The value of $\Delta I/I_{max}$ increases with increasing Trypan Blue concentration in the staining solution, from 0% up to about 0.5% by weight, after which it plateaus. The dash-dot horizontal line at a $\Delta I/I_{max}$ of about 50% indicates the threshold for visual discrimination of the edge of an anterior capsulotomy. The $\Delta I/I_{max}$ values were determined from image processing using a computer and software to determine the intensity values for manually selected samples of the image corresponding to representative lens capsules, all illuminated in a consistent manner and on a standardized red-orange background (RGB: 255, 63, 52). A white background (with microscope illumination RGB: 255, 240, 220) was used in a parallel experiment and similar trend lines are observed, with the difference that the asymptotic values relative to the background are lower for the white background. $I_{max}$ corresponds to the intensity for the background without the lens capsule stained. $\Delta I$ corresponds to the different in intensity from $I_{max}$ to that of the lens capsule stained with the concentration under investigation for 100 seconds. The visual discrimination threshold was determined by human observers reviewing microscope videos of eyes undergoing cataract surgery under standard illumination conditions. The criteria for determination of the visual discrimination was illumination conditions for cataract surgery, and the ability to discriminate the stained lens capsule compared to the center of the capsulotomy absent the crystalline lens. This figure shows that the threshold for visual discrimination of the center of the capsulotomy to the anterior capsulotomy stained with a Trypan Blue solution is a concentration of about 0.2% by weight. Visual discrimination improves further with increasing Trypan Blue concentration and thus increasing $\Delta I/I_{max}$. The visual discrimination threshold for thinner tissue such as stained posterior capsule relative to the center of the capsulotomy was determined to be 0.3% concentration by weight.

Figure 5:
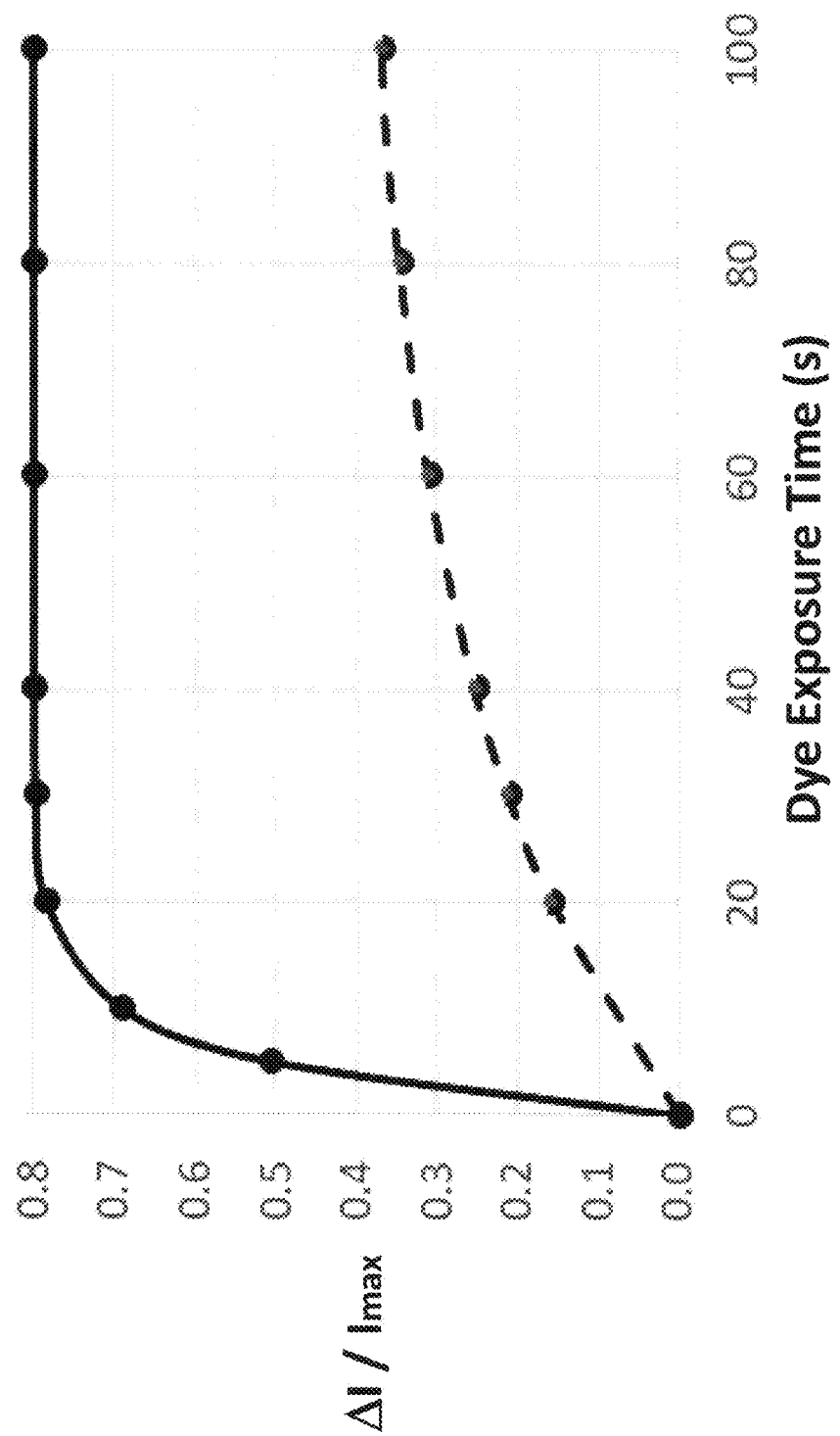
FIG. 5 plots $\Delta I/I_{max}$ versus time for staining solutions having a Trypan Blue concentration of 0.1% by weight and of 0.4% by weight.

The inventor has also experimentally determined that the rate at which the Trypan Blue solution stains the lens capsule increases with the concentration of Trypan Blue in the staining solution. FIG. 5 plots $\Delta I/I_{max}$ versus time for staining solutions having a Trypan Blue concentration of 0.1% by weight (dashed line) and of 0.4% by weight (solid line). Staining with the 0.4% solution results in a rapid rise of $\Delta I/I_{max}$ over about 20 seconds to a plateau of about 0.8. In contrast, staining with the 0.1% solution (preferred by Melles and Coroneo) results in a much slower rise of $\Delta I/I_{max}$ over about 80 seconds to a lower plateau of less than 0.4. Note this is less than half of the contrast for 0.4% solution, and at 20 seconds the ration is over 5-fold difference.

Thus, the inventor has determined that the use of a Trypan Blue solution at concentrations of 0.2 to 0.45% by weight to stain the lens capsule is advantageous compared to prior art preferred concentration of 0.1% (Melles, Coroneo discussed above), because it provides faster and darker staining and better visual discrimination while remaining safe to eye tissues.

The inventor has also experimentally determined with human and porcine eyes that the contrast between the stained portion of the lens capsule to unstained portions increases with the thickness of the stained region. This can be seen for example in FIG. 3, in which the stained anterior capsulotomy rolled-over edge 14 (30 microns thick for human, 60 microns thick for porcine) is darker than the stained anterior capsule 11 (15 microns thick for human, 30 microns thick for porcine), and the stained anterior capsule 11 is darker than the stained posterior capsule 4 (4 microns thick for humans, 6 microns thick for porcine). (FIG. 3 is an image of a porcine eye).

The inventor's experimental work implies that Trypan Blue molecules diffuse into and through the full thickness of the lens capsule. The staining rate is proportional to the concentration of Trypan Blue in the staining solution. Also, the overall dye intensity effect increases with dye concentration in the staining solution, the overall dye intensity effect increases with thickness of the stained tissue, and the Trypan Blue molecules are held in place in the collagen IV matrix of the lens capsule with temporary intermolecular bonding (likely Van der Waals bonding) allowing natural removal within a few hours.

Diffusion in to and partially through the collagen IV matrix of the lens capsule is further supported as the inventor has observed dye stained lens epithelial cell which are posterior to the anterior lens capsule utilizing Trypan Blue solutions of 0.3% or greater by weight and the staining method described above. These individual transparent cells are hard to visually identify in the absence of Trypan Blue and are responsible for some long-term complications that may occur following cataract surgery. The dye stains the living lens epithelial cells (mechanism of action is not supported in the prior art), such that as light passes through the additional stained tissue visual identified is possible due to the increased darkened appearance due to thickness of stained tissue. The surgeon would likely remove these visible stained lens epithelial cells following removal of the crystalline lens at the time of cataract surgery to reduce the probability of post-operatively complications.

Figure 6:
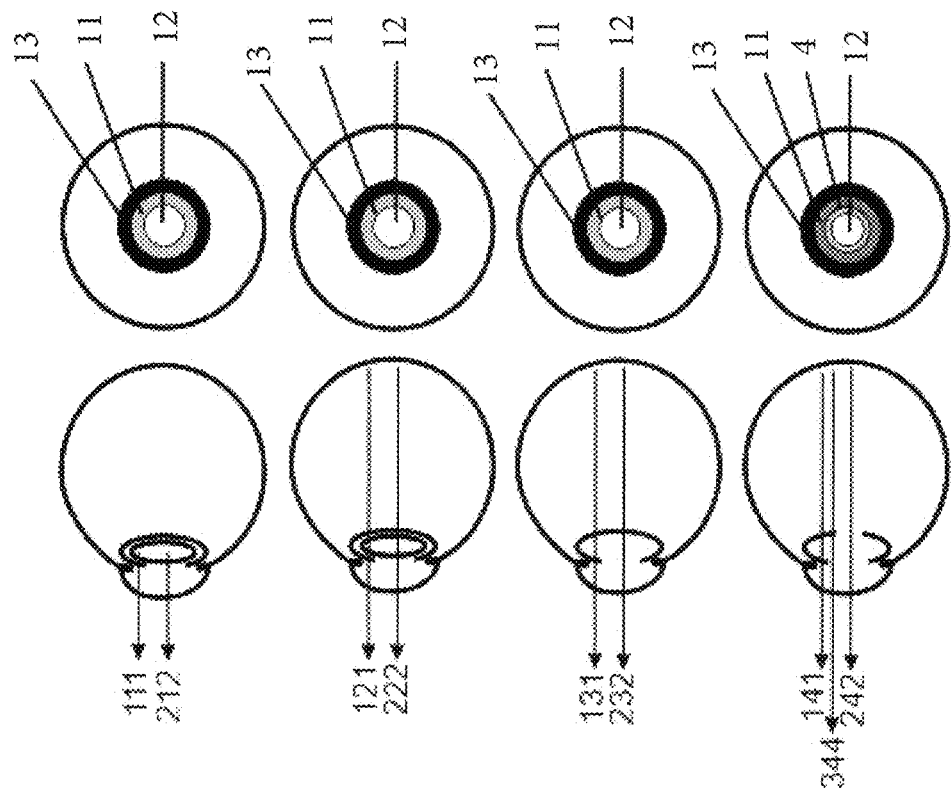
FIGS. 6A, 6B, 6C, 6D show AP and cross-sectional views of the eye for four examples in which a capsulotomy is performed.

Four example cases are described in greater detail below with respect to FIGS. 6A-6D, which show cross-sectional and AP views of an eye for each case. FIG. 6A shows example 1, in which an anterior capsulotomy has been performed on an eye having an advanced white cataract. FIG. 6B shows example 2, in which an anterior capsulotomy has been performed on an eye having a translucent cataract. FIG. 6C shows example 3, in which an anterior capsulotomy has been performed and the crystalline lens has been removed from the lens capsule. FIG. 6D shows example 4, in which anterior and posterior capsulotomies have been performed and the crystalline lens has been removed from the lens capsule.

Referring again to FIG. 6A, in example 1 the eye comprises an advanced cataract. The cataract scatters light, which decreases the amount of light reaching the retina and decreases contrast sensitivity, which reduces visual acuity of the subject and is the medical definition of a cataract. In some advanced cases the cataract scatters light both forward toward the retina and backward away from the retina. In such cases, under direct illumination with white light (from a Xenon lamp, for example), the back-scatter makes the cataract appear white. An advanced cataract may be highly opaque with a major loss of the patient's visual acuity.

Still referring to FIG. 6A, white light illumination passing through the center of the capsulotomy region 12 is incident on and back-scattered by the cataract without passing through the Trypan Blue stained capsule, so the back-scattered portion of the incident light (e.g., ray 212) is also white. White light illumination incident on Trypan Blue stained anterior capsule portion 11 enters the eye through the stained capsule, is back-scattered by the cataract, and passes again through the stained anterior capsule as it exits the eye along light ray 111. Light absorption by Trypan Blue modifies the color of the light exiting along light ray 111, because Trypan Blue strongly absorbs orange and red light, only mildly absorbs green light, and minimally absorbs blue light. The degree of modification of the light is depends on the Trypan Blue dye concentration and the thickness of the lens capsule.

Figure 7:
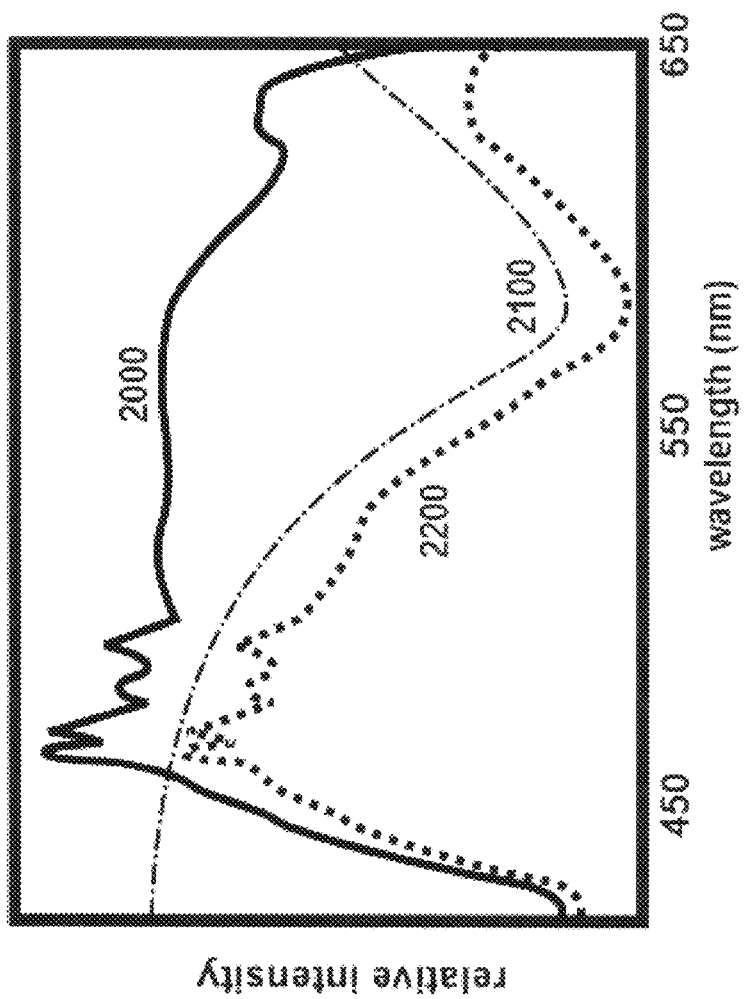
FIG. 7 shows plots of a typical Xenon bulb spectrum, the transmission spectrum of Trypan Blue, and the spectrum of light from the Xenon bulb transmitted through Trypan Blue.
Figure 8:
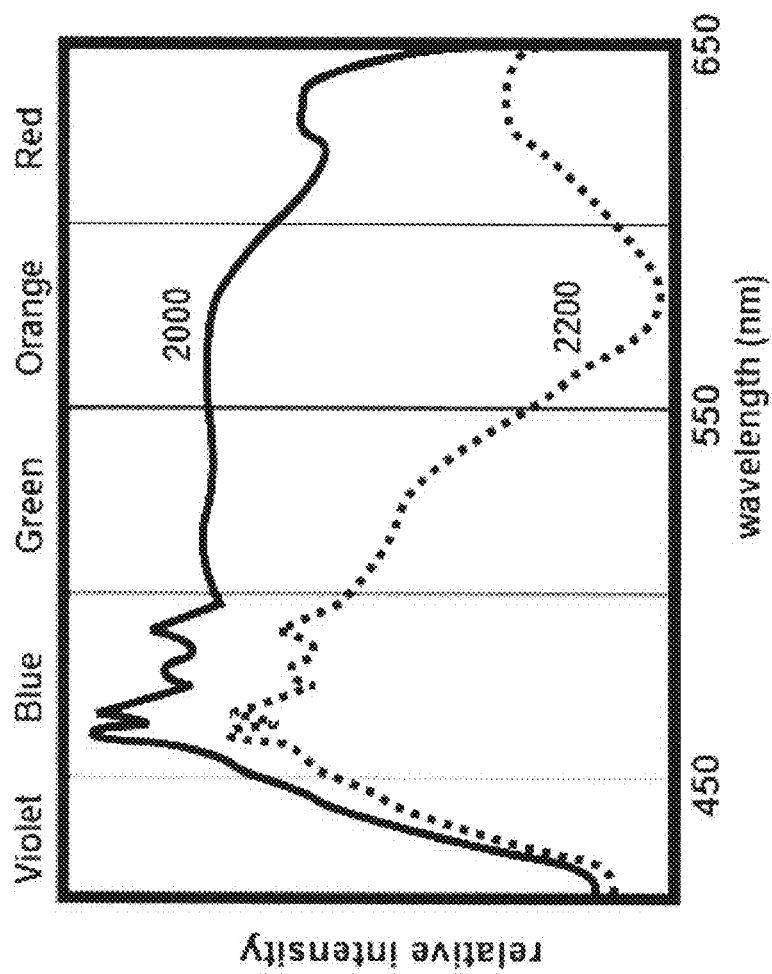
FIG. 8 shows plots of a typical Xenon bulb spectrum and the spectrum of light from the Xenon bulb transmitted through Trypan Blue.

FIG. 7 shows a typical Xenon bulb spectrum 2000 found in microscope illumination, the transmission spectrum 2100 of Trypan Blue, and the resultant transmission 2200 which is the multiplication of these two spectra. This resultant represents the light after passing through the trypan blue stained portion of the lens capsule. The spectra shown in FIG. 8 represent the difference in color and intensity between light exiting along light ray 111 (spectrum 2200) and light exiting along light ray 212 (spectrum 2000).

Figures 9A, 9B:
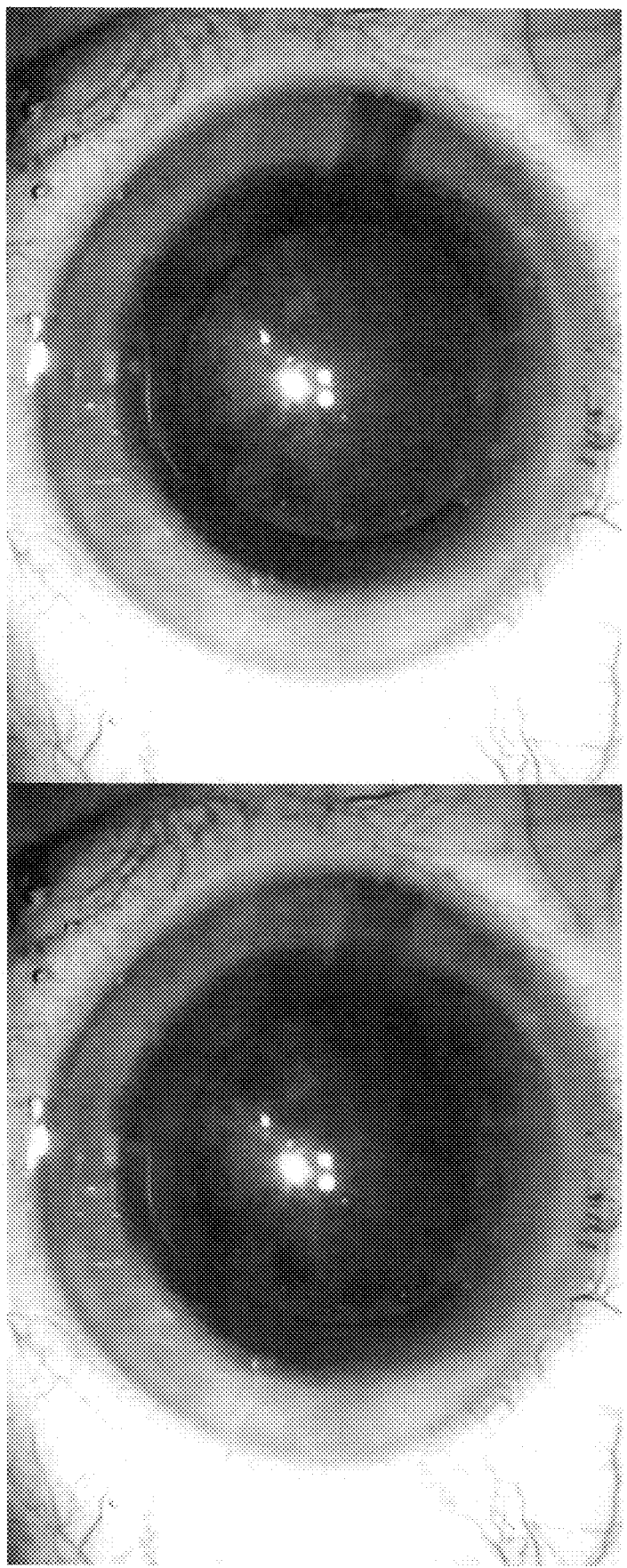
FIGS. 9A and 9B show, respectively, color and grey scale images of an eye having a Trypan Blue stained lens capsule and an advanced white cataract on which an anterior capsulotomy has been performed.

In this example a color shift is observed between regions dyed with Trypan Blue and undyed regions. The color shift occurs because the advanced cataract back-scatters white light, and the Trypan Blue absorbs in the green, orange and red and not strongly in the blue. The result is a blue appearance and less intensity in the stained region. This is apparent in the color image of FIG. 9A, for example.

Such a color shift is less apparent, or not observable, with the more general case of translucent cataracts discussed below, in which visualization is based on light reflected from the retina. As further discussed below, light reflected from the retina has a low intensity of blue light, so the effect of the Trypan Blue is to absorb and reduce the intensity of the light without significantly changing its color.

In the general case, the observed light from the stained regions of the capsule is darker with less intensity because of Trypan Blue absorption, and the view appears brighter in intensity in unstained regions of the capsule. This is apparent in FIG. 9B for example, which is a gray-scale version of the color image of FIG. 9A.

Examples 2-4 discussed below all involve the white illumination light being reflected by the retina, which changes the wavelength distribution and thus the observation characteristics. These changes to the reflected spectrum are illustrated in FIG. 10, which shows a typical Xenon bulb spectrum 2000 found in microscope illumination, the retina reflectance 2300, and the spectrum 2400 of the light from the Xenon bulb reflected from the retina, which is the product of spectrum 2000 and spectrum 2300. The retina strongly absorbs blue and green light, and the distribution of light reflected from the retina is predominantly in the red and orange with only weak intensity in the blue and green. Thus, in examples 2, 3 and 4 a major color shift is not observed. Instead, visual discrimination of tissues and tissue boundaries is based on a darkening of the light intensity for the light passing through Trypan Blue. The degree of darkening increases with dye concentration and thickness of the path through the capsule.

Retina reflectance spectrum 2300 was obtained from F. C. Delori and K. P. Pflibsen "Spectral reflectance of the human ocular fundus", APPLIED OPTICS, 28 (6) 1989. Their data was confirmed with the inventor's experimental data.

Referring again to FIG. 6B, in example 2 (anterior capsulotomy has been performed on an eye having a translucent cataract) the cataract in the crystalline lens allows light to be transmitted to the retina with degraded visual acuity, but the lens does not have a white appearance. The majority of cataracts that are surgically removed are translucent and not classified as "white cataracts", i.e. back-scatter of illuminating light is minimal to non-existent. There is a need to visualize the anterior capsule for the formation of the capsulotomy and for removal of the crystalline lens by phacoemulsification or extracapsular extraction.

In this example, white light illumination passing through the center of the capsulotomy region 12 and the crystalline lens is incident on and diffusely reflected from the retina, and the reflected light emerges from the eye along light ray 222 without passing through the capsule and thus is not modified by Trypan Blue. If the illuminating light is from a Xenon lamp, light emerging along ray 222 has the spectrum 2400 shown in FIG. 10.

White light illumination incident on Trypan Blue stained anterior capsule portion 11 enters the eye through the stained capsule, which absorbs red and orange light. The light is then incident on and diffusely reflected by the retina, which strongly absorbs blue and green light. The light reflected by the retina then passes again through the stained anterior capsule, which again absorbs red and orange light, and exits the eye along light ray 222.

Figure 11:
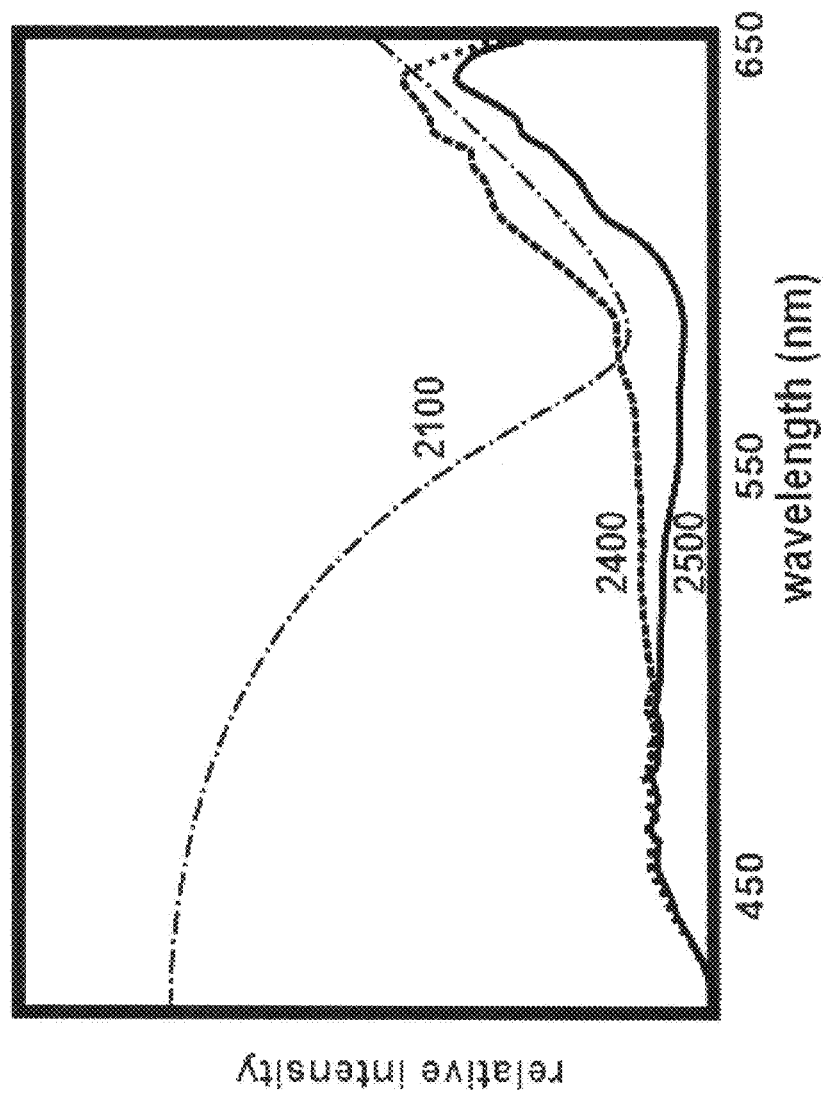
FIG. 11 shows plots of the Trypan Blue transmission spectrum, the spectrum of light from a Xenon bulb reflected from the retina, and the spectrum of light from a Xenon bulb reflected from the retina and transmitted through Trypan Blue.
Figure 12:
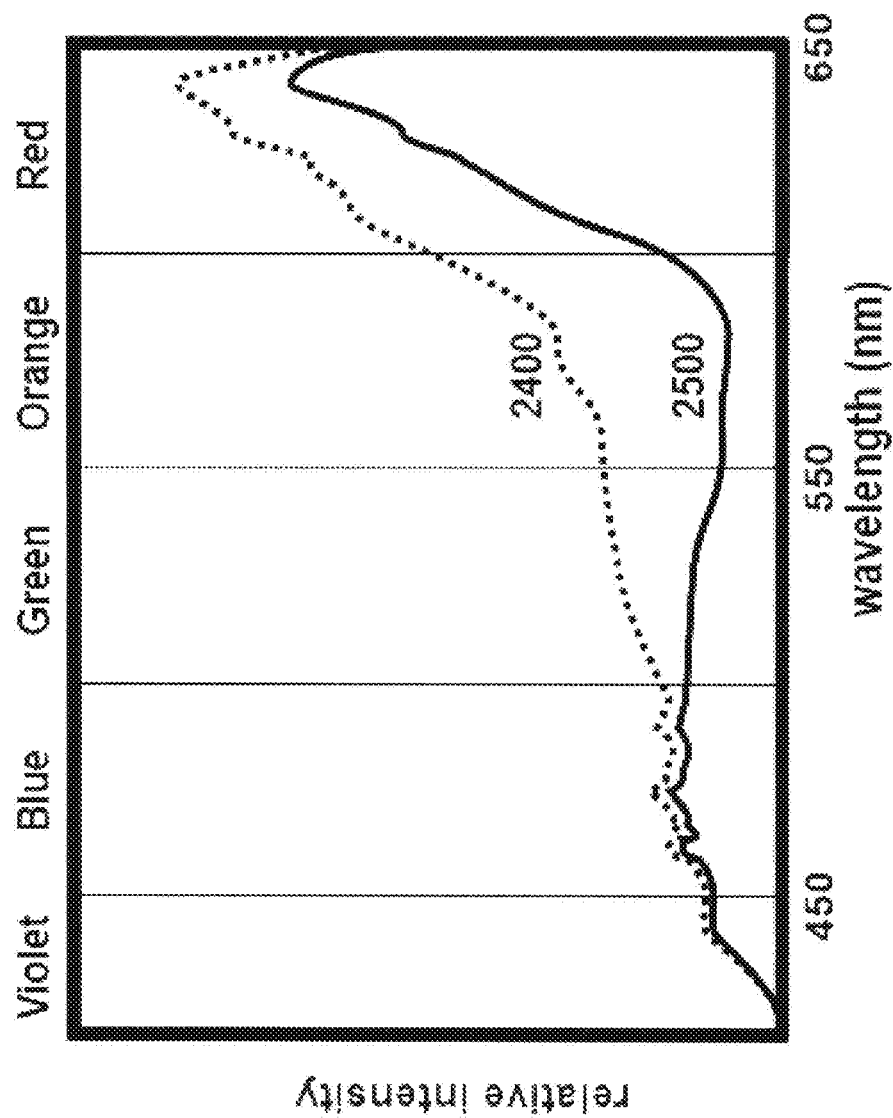
FIG. 12 shows plots of the spectrum of light from a Xenon bulb reflected from the retina, and the spectrum of light from a Xenon bulb reflected from the retina and transmitted through Trypan Blue.
Figure 13:
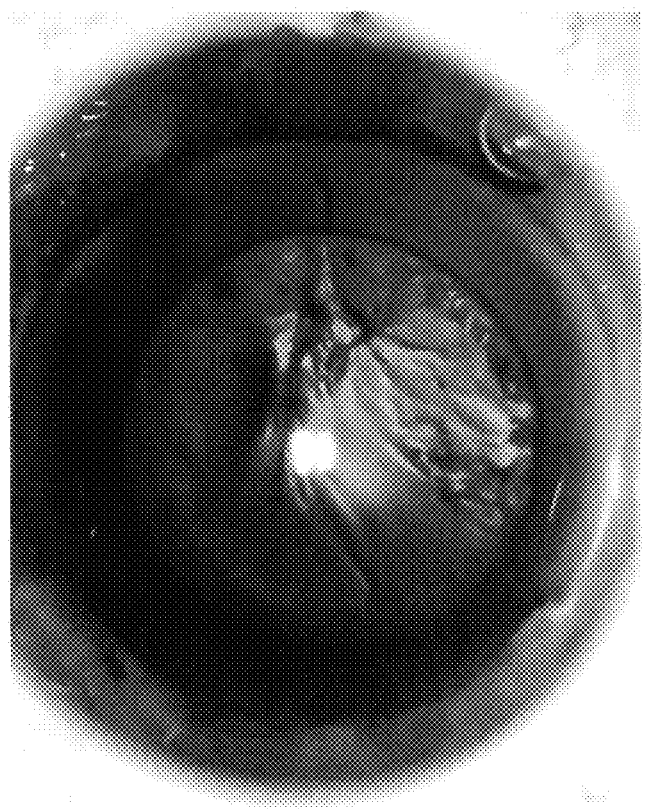
FIG. 13 is a photograph of an eye comprising a translucent cataract in which a capsulotomy has been performed in the anterior lens capsule after staining the lens capsule with Trypan Blue.

FIG. 11 shows the Trypan Blue transmission spectrum 2100, the spectrum 2400 of light from a Xenon bulb reflected from the retina, and the resulting spectrum 2500 of light exiting along ray 222. The spectra shown in FIG. 12 represent the difference in color and intensity between light exiting along light ray 121 (spectrum 2500) and light exiting along light ray 222 (spectrum 2400). As shown in the photograph of FIG. 13, there is no obvious color shift between stained and unstained regions in this example. The degree of the intensity shift depends on the concentration of the Trypan Blue solution and the thickness of the capsule the light traverses.

It should be noted that the natural crystalline lens does not have a strong absorption but in mature patients has a tendency to absorb violet and blue light. This further reduces the amount of blue light being observed.

Referring again to FIG. 6C, in example 3 an anterior capsulotomy has been performed and the crystalline lens has been removed from the lens capsule. Following removal of the crystalline lens almost all eyes have a similar appearance in surgery, independent of whether the cataract was white or translucent. The condition of the retina may affect the coloration slightly. In many ways this example has a similar optical description to Example 2. There is a need to visualize the anterior capsule and the capsulotomy boundary for cortical clean up and insertion of an artificial IOL.

In this example, white light illumination passing through the center of the capsulotomy region 12 is incident on and diffusely reflected from the retina, and the reflected light emerges from the eye along light ray 232 without passing through the capsule and thus is not modified by Trypan Blue. If the illuminating light is from a Xenon lamp, light emerging along ray 232 has the spectrum 2400 shown in FIG. 10 and FIG. 11.

Figure 14:
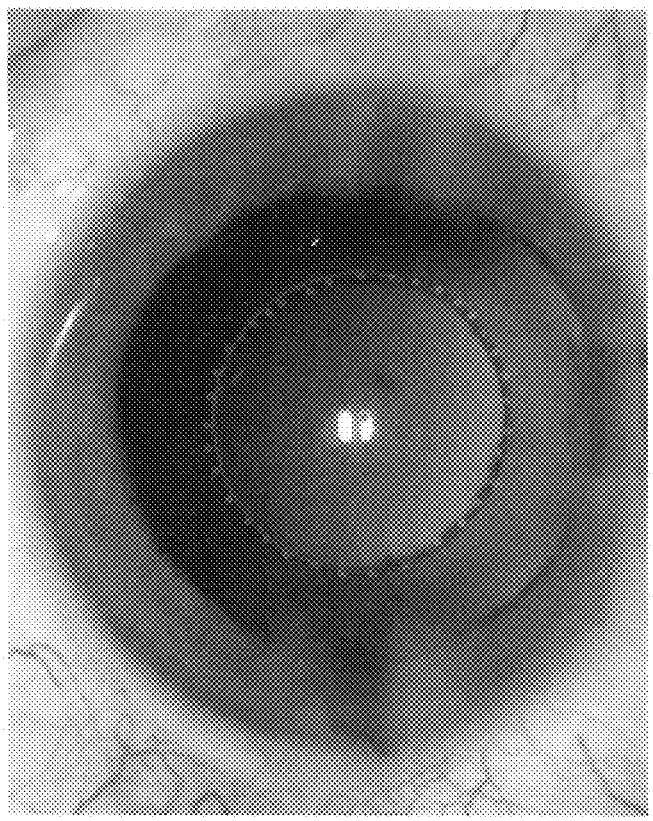
FIG. 14 is a photograph of an eye in which an anterior capsulotomy has been performed and the crystalline lens removed from the lens capsule after staining the lens capsule with Trypan Blue.

White light illumination incident on Trypan Blue stained anterior capsule portion 11 enters the eye through the stained capsule, which absorbs red and orange light. The light is then incident on and diffusely reflected by the retina, which strongly absorbs blue and green light. The light reflected by the retina then passes again through the stained anterior capsule, which again absorbs red and orange light, and exits the eye along light ray 131. Light exiting along ray 131 has spectrum 2500 shown in FIG. 11. The spectra shown in FIG. 12 represent the difference in color and intensity between light exiting along light ray 131 (spectrum 2500) and light exiting along light ray 232 (spectrum 2400). As shown in the photograph of FIG. 14, there is no obvious color shift between stained and unstained regions in this example. The degree of the intensity shift depends on the concentration of the trypan blue solution and the thickness of the capsule the light traverses.

Referring again to FIG. 6D, in example 4 anterior and posterior capsulotomies have been performed and the crystalline lens has been removed from the lens capsule. The posterior capsule is very thin and elastic. The use of trypan blue or an alternative dye is critical for visualization. There is a need to visualize the posterior capsule and the capsulotomy boundary for the formation of the posterior capsulotomy, and any subsequent surgery.

In this example, white light illumination passing through the center of the capsulotomy region 12 is incident on and diffusely reflected from the retina, and the reflected light emerges from the eye along light ray 242 without passing through the capsule and thus is not modified by Trypan Blue. If the illuminating light is from a Xenon lamp, light emerging along ray 242 has the spectrum 2400 shown in FIG. 10 and FIG. 11.

White light illumination incident on Trypan Blue stained posterior capsule portion 4 passes through the stained posterior capsule, which slightly absorbs red and orange light. The light is then incident on and diffusely reflected by the retina, which strongly absorbs blue and green light. The light reflected by the retina then passes again through the stained posterior capsule, which again slightly absorbs red and orange light, and exits the eye along light ray 344.

White light illumination incident on Trypan Blue stained anterior capsule portion 11 enters the eye through the stained anterior capsule, which absorbs red and orange light. The light then passes through the stained posterior capsule, which slightly absorbs red and orange light, then is incident on and diffusely reflected by the retina, which strongly absorbs blue and green light. The light reflected by the retina again passes through the stained posterior capsule, which again slightly absorbs red and orange light, then again through the stained anterior capsule which again absorbs red and orange light, then exits the eye along ray 141.

Light emerging along rays 344 and 141 will have similar spectra (e.g., spectrum 2500). The net observable difference between light along rays 141, 344, and 242 is intensity, where light along ray 141 is darker, light along 344 has intermediate intensity, and light along 242 has maximum intensity from the retina reflection. The degree of the intensity shift depends on the concentration of the trypan blue solution and the thickness of the capsule that the light traverses. There is no obvious color shift between stained and unstained regions in this example.

The examples described above use a Trypan Blue solution of 0.2% to 0.45%. Other variations may use multiple dyes dissolved in a common solvent to create a solution with an accumulated concentration in the range of 0.2 to 0.45% to absorb in the red and orange region of the spectrum with a similar or greater magnitude to that of a 0.2% Trypan Blue solution. For example, Trypan Blue 0.15% in combination with Evans Blue 0.15%. The masses of these diazo dyes are somewhat similar in mass and light absorption to each, thus the combined concentration by weight of 0.2 to 0.45% is expected to yield similar results.

In addition to the uses described above, the Trypan Blue solutions describe herein may be used to increase visualization of corneal and limbal incisions.

The ophthalmic dye solutions of the present invention may be used to enhance identification and visualization of the lens capsule and capsulotomy boundary in cataract surgery methods employing direct observation of the lens capsule by a human observer, e.g. through a stereoscopic microscope, and/or by machine vision guided cataract surgery methods utilizing video cameras or other imaging devices and automated anatomical recognition. The intensity change between stained capsule regions and the capsulotomy region allows for the use of this invention with algorithms employing image intensity processing and anatomical recognition of the pupil-iris and/or limbus-iris boundary to allow calculation of the capsulotomy boundary location and determination of the tissue location. Such machine vision may be used in addition to or in combination with a conventional stereoscopic microscope. A robotic cataract surgical device can perform cataract surgery with information on anterior capsule location and its capsulotomy on a regular rate of, for example, at least 10 Hz to insert and perform phacoemulsification of the natural crystalline lens, cortical clean-up with irrigation and aspiration, removal of lens epithelial cells, formation of a posterior capsulotomy insertion and positioning of the IOL into the lens capsule.

Figure 15:
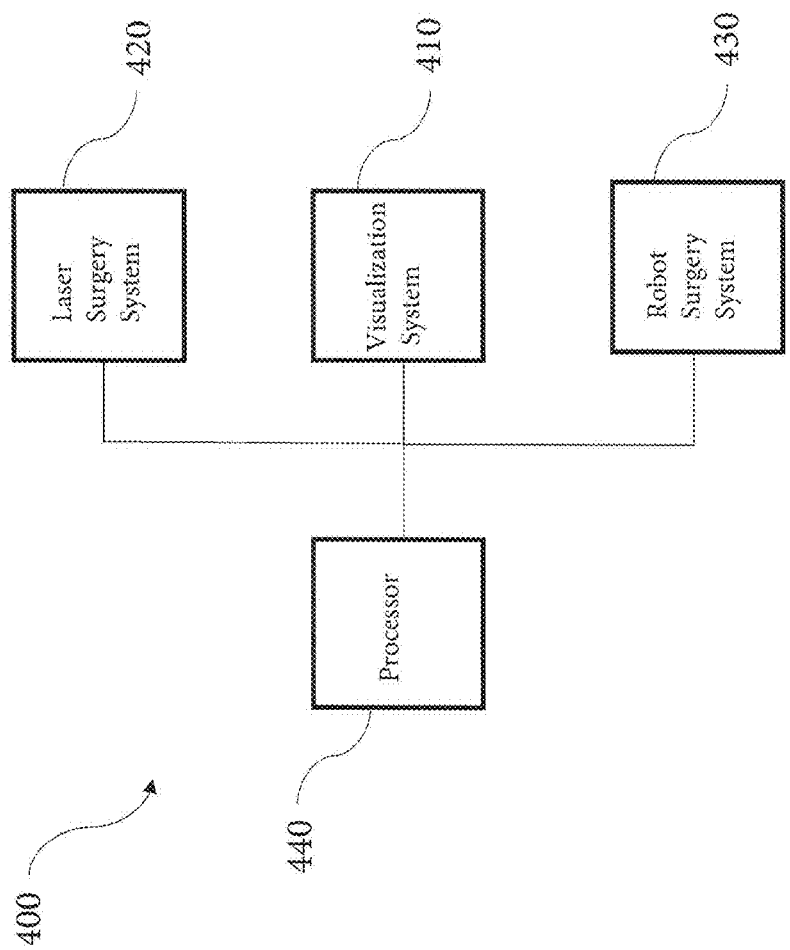
FIG. 15 shows a schematic diagram of an example cataract surgery system.

FIG. 15 shows a schematic diagram of an example cataract surgery system 400 that may be employed with the dye solutions and related methods described herein with enhanced visualization. System 400 comprises a visualization system 410, an optional surgical laser system 420, an optional robot surgical system 430, and an optional processor 440. Visualization system 410 may be used by a human surgeon or by a robotic surgical system to view the lens capsule and other portions of the surgical field during cataract surgery. Visualization system 410 may comprise, for example, a stereoscopic microscope as conventionally employed in ophthalmic surgery, an imaging system including a camera or other imaging device, or a microscope and a camera or other imaging device. In variations in which cataract surgery is performed using laser ophthalmic surgical methods, system 400 may comprise an optional ophthalmic surgical laser system 420. Portions of the optical path of surgical laser system 420, if present, may optionally be integrated into an optical path of visualization system 410. In variations in which cataract surgery is robotically assisted or performed, system 400 may comprise robot surgical system 430 which may perform as described above, for example. System 400 may comprise a processor 440 in communication with any or all of visualization system 410, laser system 420, and robot surgical system 430. Processor 440 may, for example, collect and analyze images from the visualization system, analyze them as described above, and control laser system 420 and/or robot surgical system 430 to assist or perform cataract surgery.

This disclosure is illustrative and not limiting. Further modifications will be apparent to one skilled in the art in light of this disclosure and are intended to fall within the scope of the appended claims.

What is claimed is:

1. A method to enhance visualization of tissues and boundaries of openings in tissues in an eye during cataract surgery, the method comprising:
providing or obtaining an ophthalmic solution comprising an isotonic and pH neutral aqueous solution of Trypan Blue at a concentration of 0.3% to 0.45% by weight;
applying the ophthalmic solution to lens capsule tissue in the eye for a time period of less than or equal to one minute to stain the lens capsule tissue with Trypan Blue; and
rinsing the ophthalmic solution from the eye.

2. The method of claim 1, wherein the ophthalmic solution is applied to the lens capsule for a time period of less than or equal to 10 seconds.

3. The method of claim 2, wherein the stained lens capsule tissue transmits less than or equal to 50% of light reflected from the retina.

4. The method of claim 3, wherein the eye comprises a translucent cataract.

5. The method of claim 1, comprising:
distinguishing between the stained lens capsule tissue and another tissue based on the intensities of light reflected from the retina of the eye through the two tissues; or
distinguishing between the stained lens capsule tissue in the lens capsule and an opening in that tissue based on the intensities of light reflected from the retina of the eye through that tissue and through the opening in that tissue; or
distinguishing between the stained lens capsule tissue and another tissue based on the intensities of light reflected from the retina of the eye through the two tissues and distinguishing between the stained lens capsule tissue in the lens capsule and an opening in that tissue based on the intensities of light reflected from the retina of the eye through that tissue and through the opening in that tissue.

6. The method of claim 5, wherein the distinguishing is done visually by a human observer viewing the lens capsule.

7. The method of claim 5, wherein the distinguishing comprises use of a machine vision system that images the lens capsule, determines intensity variations in the image, and utilizes anatomical recognition algorithms to determine the location in the image of a capsulotomy boundary in the lens capsule.

8. The method of claim 7, wherein the anterior lens capsule location is identified, and this information used to guide robotic surgery to perform at least one of the following functions: placement and movement of a phacoemulsification hand piece to remove the natural crystalline lens, placement and movement of an irrigation and/or aspiration cannula to remove lens cortical, placement and movement of an irrigation and/or aspiration cannula to remove lens epithelial cells, operation of a laser system for the formation of a posterior capsulotomy, and guiding placement and movement of an artificial IOL during insertion and positioning in to the lens capsule.

9. The method of claim 5, wherein lens epithelial cells are identified.

10. The method of claim 1, comprising:
following capsulotomy and removal of the natural crystalline lens, distinguishing between the lens capsule tissue stained by Trypan Blue and an opening in that tissue.

11. The method of claim 1, comprising:
following capsulotomy and removal of the natural crystalline lens, identifying lens epithelial cells stained by Trypan Blue.

12. The method of claim 1, comprising:
following capsulotomy and removal of the natural crystalline lens, distinguishing between anterior lens capsule tissue stained by Trypan Blue, posterior lens capsule stained by Trypan Blue, and openings in those tissues.

* * * * *

UNITED STATES PATENT AND TRADEMARK OFFICE
CERTIFICATE OF CORRECTION

PATENT NO. : 11,260,135 B2  
APPLICATION NO. : 15/953310  
DATED : March 1, 2022  
INVENTOR(S) : David Mordaunt Page 1 of 1

It is certified that error appears in the above-identified patent and that said Letters Patent is hereby corrected as shown below:

On the Title Page

(71) Applicant should read: EXCEL-LENS, INC., Los Gatos, CA (US)

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*